United States Patent [19]

Hynecek et al.

[11] 4,023,562
[45] May 17, 1977

[54] MINIATURE PRESSURE TRANSDUCER FOR MEDICAL USE AND ASSEMBLY METHOD

[75] Inventors: Jaroslav Hynecek, Bedford; Wen H. Ko, Cleveland Heights; Eugene T. Yon, Lyndhurst, all of Ohio

[73] Assignee: Case Western Reserve University, Cleveland, Ohio

[22] Filed: Sept. 2, 1975

[21] Appl. No.: 609,382

[52] U.S. Cl. ............................ 128/2.05 E; 29/577; 29/580; 73/398 R; 73/408; 73/420
[51] Int. Cl.² .......................................... A61B 5/02
[58] Field of Search ............. 128/2 R, 2 S, 2.05 D, 128/2.05 E, 2.05 P, 2.06 E, 2.05 R, 2 P; 73/398 R, 406, 408, 420, DIG. 4; 29/577, 580, 590, 613, 25.35

[56] References Cited

UNITED STATES PATENTS

| 3,154,067 | 10/1964 | Stenstrom et al. | 128/2.05 P |
|---|---|---|---|
| 3,572,322 | 3/1971 | Wade | 128/2.06 E |
| 3,592,187 | 7/1971 | Youdin et al. | 128/2.05 E |
| 3,858,150 | 12/1974 | Gurtler et al. | 29/580 |
| 3,909,924 | 10/1975 | Vindasios et al. | 29/580 |
| 3,943,915 | 3/1976 | Severson | 128/2.05 E |

OTHER PUBLICATIONS

DeLaunois "Medical and Biological Engineering", vol. 12, No. 3, May, 1974, pp. 364–365.

Primary Examiner—William E. Kamm
Attorney, Agent, or Firm—McNenny, Pearne, Gordon, Gail, Dickinson & Schiller

[57] ABSTRACT

A fluidtight, hermetically sealed, miniature transducer adapted to be inserted into the human body and useful for directly monitoring internal fluid or pneumatic pressures within the human body is disclosed. Semiconductor strain gauge elements constituting a piezoresistive bridge are formed by diffusion on the surface of one side of an integral flexible, rectangular, silicon diaphragm area of a single crystal silicon base. A single crystal silicon cover is eutectically bonded to the base by a metallic laminate seal. The base, cover, and seal define an evacuated fluidtight chamber containing the strain gauge elements. Electrical conductors, which include diffused conductor paths under an insulating oxide layer, extend from the piezoresistive bridge to contact pads outside the fluidtight chamber. The contact pads can be connected to a readout device for electrically measuring the pressure differential between the evacuated chamber and fluid external to the transducer as a function of time.

10 Claims, 3 Drawing Figures

MINIATURE PRESSURE TRANSDUCER FOR MEDICAL USE AND ASSEMBLY METHOD

BACKGROUND OF THE INVENTION

The present invention is in the field of diffused strain gauge pressure transducers.

More particularly, the present invention relates to miniaturized pressure transducers capable of being implanted within the human or animal body for direct measurement of physiological pressures, such as respiratory, venous, arterial, amniotic, and cerebrospinal fluid pressures. Prior art transducers capable of monitoring physiological pressures in human beings and animals were normally not implanted in the body due to their undesirably large size, fragility, and complexity. These transducers were usually connected to the pressure source monitored by a fluid-filled catheter inserted into the body. This method of monitoring pressure often resulted in unreliable and inaccurate data, due to dynamic response problems associated with the fluid-filled catheter.

Attempts to implant miniaturized pressure transducers within the body for direct measurement of internal fluid pressure often resulted in malfunctions due to leakage of body fluid into the critical components of the transducer.

SUMMARY OF THE INVENTION

The present invention provides a miniaturized, fluid-tight pressure transducer capable of being implanted within a human or animal body. All components of the transducer are hermetically bonded together to provide a rugged, reliable sensor package. The transducer is assembled using known microcircuitry techniques, resulting in a finished pressure sensor measuring approximately 1.25 by 3.75 mm. with a depth of 0.250 mm.

An N-type, phosphorus-doped, single crystal, silicon base and a single crystal silicon cover are eutectically bonded together by a metallic laminate seal in a vacuum environment to form an evacuated, fluidtight pressure reference chamber which contains piezoresistive bridge sensor elements diffused on a flexible diaphragm formed by preferential etching of the crystal silicon base of specific crystalline orientation.

The diaphragm will flex or deform when there is a fluctuation of the pressure differential between the sealed pressure reference chamber and fluid external to the implanted pressure transducer. As the diaphragm flexes, the electrical parameters of the piezoresistive bridge will change proportionately. Electrical conductors lead from the piezoresistive bridge to a set of contacts external to the sealed reference chamber. These electrical conductors take the form of diffused, electrically insulated conductor paths on the surface of the silicon base where the conductors exit the evacuated chamber.

Conventional electrical readout circuitry can be connected to the external transducer contacts to monitor and record fluid pressure, represented by the electrical parameters of the piezoresistive bridge. When utilized with an active temperature compensation circuit, the transducer can provide a linear output proportional to pressure that is stable to better than 1 mm. Hg at a 300 mm. Hg of full scale range, from room temperature to 40° C.

The use of silicon, which is an essentially perfect elastic material, provides a transducer having excellent time stability and linear response with minimal hysteresis. The maximum width of the temperature hysteresis curve of the illustrated transducer is better than 3 mm. Hg when cycled between 10° and 40° C.

The pressure sensitivity of the transducer is approximately 0.033 millivolts per mm. Hg, with an uncompensated temperature drift of ± 5.2 mm. Hg/° C. By providing temperature compensation, a reduction of temperature drift to ± 0.1 mm. Hg/° C. is obtained consistently.

DESCRIPTION OF THE PREFERRED EMBODIMENT

Figure 1:
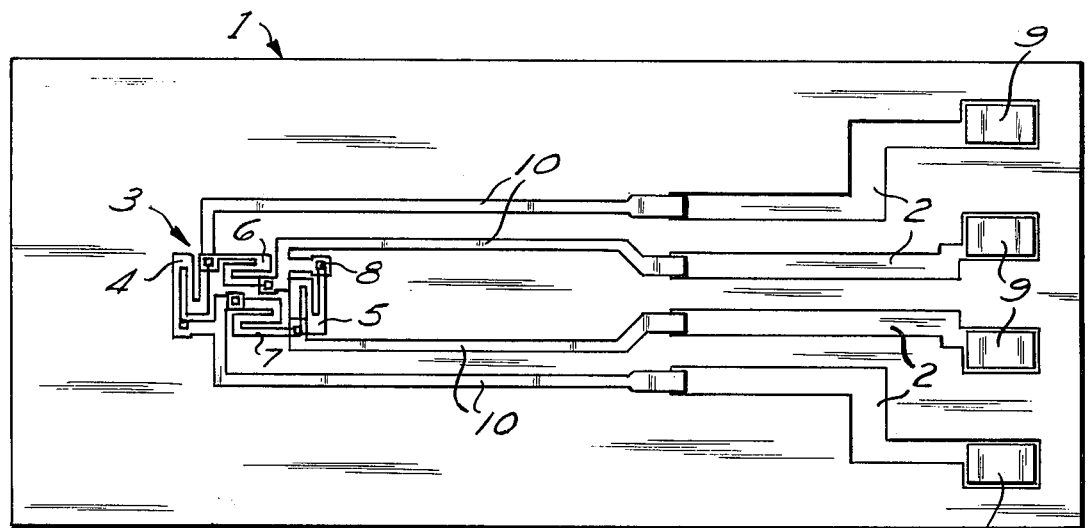
FIG. 1 is an enlarged, not-to-scale, plan view of the preferred embodiment of the pressure transducer according to the present invention, showing the base member and its components with the cover removed.

Referring now to the drawing, and more particularly to FIG. 1, there is shown a plan view of a single crystal, silicon semiconductor base 1 which is generally rectangular in shape. The waferlike base 1 is produced by means well known to the semiconductor art, for example, by growing a large, single crystal in a melt of silica which contains a doping agent such as arsenic or phosphorus. This large crystal is then sliced and cut into thin wafers which can then be lapped to the desired thickness and etched in an appropriate silicon etching bath to remove surface defects.

In the preferred embodiment of the invention, the semiconductor base material is phosphorus-doped silicon having N-type conductivity characteristics. This silicon transducer base cut from a single crystal measures approximately 3.75 mm. in length and 1.25 mm. in width, and has a depth of approximately 0.125 mm. The molecular orientation of the illustrated silicon crystal is measured by well known X-ray diffraction techniques. This orientation measurement is usually specified by the silicon wafer supplier or manufacturer. For example, the illustrated base is formed of monocrystalline silicon cut along the [100] crystallographic plane.

In assembling the pressure transducer, the single crystal silicon base is first polished on both sides. Then, by a wet oxidation process, an initial layer of silicon dioxide is grown on both sides of the base to a thickness of approximately 1000 angstroms (A).

Using well known microcircuitry design techniques such as those utilized in the production of integrated circuits, the base 1 is then photolithographically processed on both sides to provide reference alignment marks and circuit patterns (not shown) for proper placement and formation of the transducer components.

The remaining components shown in FIG. 1 can be formed, using well known chemical techniques such as etching, reoxidation, metalization, and diffusion and/or epitaxial growth methods.

In the preferred embodiment, four diffused conductor paths 2 are formed on the top surface of the silicon base 1. The windows for these conductor paths are etched in the $SiO_2$ layer. The base 1 is then placed into a diffusion furnace containing a P-type dopant such as boron and heated, to vapor-diffuse boron into the silicon base 1 of the exposed conductor paths 2. The depth of penetration of the boron into the surface of the conductor paths 2 is a function of time and temperature, and is well known in the art. The depth of the boron-diffused conductor paths 2 is such that the conductor paths have a relatively low resistance.

The remaining $SiO_2$ is etched away and the base 1, with its diffused conductor paths 2, is again oxidized with a layer of $SiO_2$.

After further photolithographic processing, windows are etched for a piezoresistive bridge 3. This bridge is composed of four interconnected resistor legs 4, 5, 6, and 7 which are formed on the exposed surface of the silicon base by the boron diffuser process, as noted above. These resistor legs are desirably extremely thin, of the order of 0.0003 to 0.003 mm. in thickness, thereby giving high resistance per unit length and permitting small physical size.

During the diffusion drive-in period for the piezoresistive bridge 3, $SiO_2$ is grown on the upper surface of the base to cover the diffused piezoresistive bridge 3. Thus, both the diffused conductor path 2 and the diffused piezoresistive bridge 3 are protected and insulated by a layer of $SiO_2$ 11 having a depth of approximately 1000 A, shown most clearly in FIG. 2. An $SiO_2$ layer 11a represents the initial $SiO_2$ layer, which of course is not subjected to etching operations.

The base 1 is again photolithographically processed. Then windows are opened by etching. These contact windows are metalized to form electrical contacts 8 (shown more clearly in FIG. 2) by vapor deposition in a vacuum chamber of a chrome-gold laminate layer having an interface with alloy characteristics with the chrome layer nearest the semiconductor surface. This technique is well known in the art.

Metalized conductor leads 10 of chrome-gold are simultaneously provided on top of the insulating layer $SiO_2$ layer 11 to connect the bridge 3 to one end of the diffused conductor paths 2. Metalized conductor pads 9 of chrome-gold are also formed at the other end of the conductor paths 2. Thus, the bridge 3 is electrically connected to the external transducer contact pads 9 via metalized contacts 8, diffused conductor paths 2, and metalized conductor leads 10. To enhance conductvity, all exposed metalized areas are then gold-plated.

Figure 2:
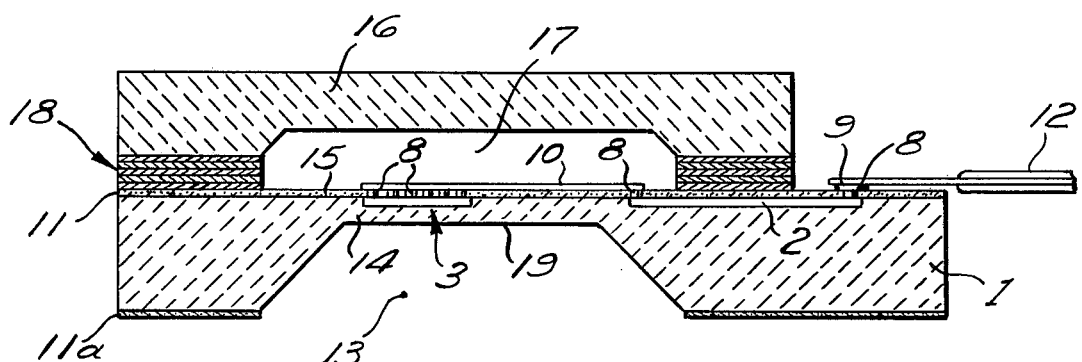
FIG. 2 is a cross sectional, elevational view, showing a complete transducer with the laminate seal layers greatly enlarged.

External readout equipment (not shown) is connected to the external transducer contacts 9 by the wires 12 (FIG. 2).

Turning now to FIG. 2, a rectangular cavity 13 is preferentially etched in the underside of the silicon base 1, resulting in a rectangular flexible diaphragm 14. The diaphragm 14 can be made extremely thin, on the order of 0.012 to 0.025 mm., due to the excellent strength and elasticity of silicon. The illustrated diaphragm area has a length of approximately 3 mm. and a width of 0.75 mm. A rectangle ratio of approximately 3:1 is preferred to provide the desired electrical sensitivity of the bridge 3. As shown in FIGS. 1 and 2, the piezoresistive bridge 3 is located in the center of the the upper surface 15 of the rectangular diaphragm 14. Alternatively, the piezoresistive bridge 3 could be located at other areas on the upper surface of the diaphragm. As is known in the art, the geometric arrangement and placement of the resistor legs 4–7 on the upper surface 15 of the diaphragm 14, the shape of the diaphragm, and the molecular orientation of the crystal base 1 are factors which determine whether a particular resistor leg will be placed under tension or compression when the diaphragms flex. This provides the desired electrical characteristics of the bridge. For example, the pair of resistor legs 4 and 5 of the bridge 3 are disposed on the surface in like geometric orientation. Resistor legs 6 and 7 are disposed in like geometric orientation to each other, but are opposed geometrically to resistor legs 4 and 5. As the diaphragm flexes, one pair of resistor legs will increase in resistance, while the opposing pair will decrease in resistance. As is known in the art, such an arrangement provides increased sensitivity in the bridge circuit.

A generally rectangular, single crystal, silicon, cup-shaped cover 16, formed by the chemical techniques noted above, is center-mounted over the upper surface of the diaphragm area, providing a chamber 17 when it is bonded to the silicon base member 1 by a laminate seal 18 (shown greatly expanded). The illustrated cover 16 has a length of 3 mm. and a width of 1.25 mm., with an edge depth of 0.125 mm. The length and width of the chamber 17 defined by the cover 16 is approximately equal to the length and width of the diaphragm 14. The depth of the chamber can be 0.1 to 0.05 mm., leaving a chamber ceiling depth of 0.025 to 0.075 mm.

The silicon base 1 and cover 16 are hermetically sealed together in a vacuum by the laminate seal 18. The fluidtight chamber 17, preferably a vacuum or partial vacuum, acts as a constant pressure reference, thus enabling pressure measurement in terms of absolute pressure as opposed to atmospheric pressure. The deformation of the diaphragm 14 will change if there is a fluctuation of the pressure differential between the sealed pressure reference chamber 17 and fluid external to the pressure transducer and in contact with the outer surface 19 of the diaphragm 14.

Figure 3:
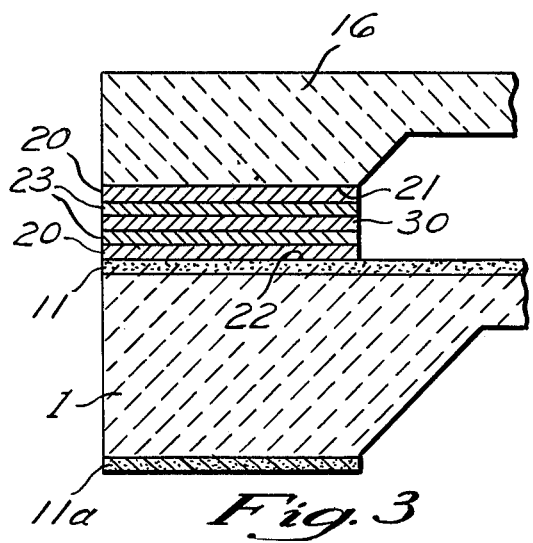
FIG. 3 is an enlarged sectional view of the laminate seal illustrated in FIG. 2.

FIG. 3 shows the laminate seal greatly enlarged. Continuous metalized strips of chrome-gold laminate 20 are deposited, using the method previously described, on a cup lip surface 21 of the rectangular cover 16 and in a corresponding rectangular configuration on an upper surface 22 of the $SiO_2$ layer 11 of the base 1 circumscribing the piezoresistive bridge 3 and crossing the conductor paths 2. The metalized strips 20 on both the base 1 and the cover 16 are then plated with layers of gold 23.

A eutectic seal 30 composed of a gold base tin alloy having a eutectic point of approximately 310° C. is used to bond the gold layers 23 together. The eutectic seal is cut from a 0.05 mm. thick sheet of a gold-tin alloy (78 w/o Au-22 w/o Sn) in the form of a rectangular gasket corresponding in size to the gold-plated, metalized strips 20 on the cover lip 21 and base 1. The cover 16 and base 1 are aligned and clamped together with the eutectic seal 30 interposed between them.

The transducer is then placed in a vacuum chamber. A vacuum is drawn, evacuating the reference chamber 17, and the transducer is heated to the eutectic point of the seal 22. The seal melts and bonds the cover 16 and base 1 together. With the vacuum maintained, the transducer is cooled and the eutectic seal 30 solidifies, hermetically sealing the cover to the base in a fluidtight relation and thus ensuring the integrity of the evacuated reference chamber 17.

The reference chamber is evacuated to avoid problems associated with temperature variations which could result from a gas-filled reference chamber due to the effect of thermal expansion and contraction of the gas on the diaphragm. It is desirable that the base 1 and cover 16 be composed of identical material to avoid any bonding problems arising from differences in their thermal coefficients of expansion and contraction.

The completed transducer is impervious to body fluid and can, because of its small size, be easily transplanted within the human body to directly monitor internal fluid pressures. For example, the transducer, because of its small size, can be inserted into an active vein or artery for direct monitoring of blood pressure.

While the transducer is ideally suited for medical use, it also has application in industrial arts where there is a need for an extremely small and rugged transducer.

Although preferred embodiments of this invention are illustrated, it is to be understood that various modifications and rearrangements of parts may be resorted to without departing from the scope of the invention disclosed and claimed herein.

What is claimed is:

1. A transducer for measuring fluid or pneumatic pressure comprising a semiconductor base member, at least a portion of said base member being a thin flexible diaphragm, a piezoresistive bridge formed on a surface of a side of said diaphragm, said bridge having at least one electrical parameter which changes in response to flexing of said surface of said diaphragm, a cover member, a seal bonding said cover member to said base member, said members and said seal defining a fluidtight chamber containing said piezoresistive bridge, and electrical conductor means extending from said piezoresistive bridge to a point external to said fluidtight chamber, said conductor means including diffused conductor paths on said base member where said conductor means passes from said fluidtight chamber to said point external to said fluidtight chamber.

2. A transducer according to claim 1, wherein said base member and said cover member have generally identical thermal coefficients of expansion and contraction.

3. A transducer according to claim 2, wherein said fluidtight chamber is evacuated.

4. A transducer according to claim 3, wherein said seal and said base member are separated by a layer of electrical insulation material.

5. A transducer according to claim 4, wherein said insulation material covers said piezoresistive bridge and said conductor paths.

6. A transducer for measuring fluid or pneumatic pressure comprising a single crystal, silicon base member with an integral flexible diaphragm, a diffused piezoresistive bridge formed on a surface of said diaphragm, said bridge having at least one electrical parameter which changes in response to the deformation of said surface of said diaphragm, a single crystal, silicon cover member, a laminate seal bonding said cover member to said base member, said members and said seal defining an evacuated fluidtight chamber containing said piezoresistive bridge, and electrical conductor means extending from said piezoresistive bridge to a point external to said fluidtight chamber, said conductor means including diffused conductor paths on said base member where said conductor means passes from said fluidtight chamber to said point external to said fluidtight chamber.

7. A transducer according to claim 6, wherein said diaphragm is rectangular.

8. A transducer according to claim 7, wherein said diaphragm has a rectangle ratio of approximately 3:1.

9. A transducer according to claim 6, wherein said laminate seal includes at least one metal alloy which eutectically bonds said cover member and said base member together.

10. A method of assembling a pressure transducer comprising the steps of:
    forming a piezoresistive bridge and diffused conductor paths on the surface of one side of a generally planar semiconductor base member, at least a portion of said base member being a thin flexible diaphragm, said bridge having at least one electrical parameter which changes in response to flexing of diaphragm;
    electrically connecting said piezoresistive bridge to one end of said diffused conductor paths;
    forming a cup-shaped cover member, said cup member being composed of semiconductor material identical to that of the base member; and
    eutectically bonding said members together with a metallic alloy seal such that said piezoresistive bridge is enclosed in a fluidtight evacuated chamber with said conductor paths extending from said fluidtight chamber to a point external to said fluidtight chamber.

* * * * *